(12) United States Patent
Reusch

(10) Patent No.: US 10,483,009 B2
(45) Date of Patent: Nov. 19, 2019

(54) DYNAMIC BEAM SHAPER

(71) Applicant: KONINKLIJKE PHILIPS N.V., Eindhoven (NL)

(72) Inventor: Tobias Reusch, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 246 days.

(21) Appl. No.: 15/520,084

(22) PCT Filed: Sep. 30, 2015

(86) PCT No.: PCT/EP2015/072502
§ 371 (c)(1),
(2) Date: Apr. 19, 2017

(87) PCT Pub. No.: WO2016/062504
PCT Pub. Date: Apr. 28, 2016

(65) Prior Publication Data
US 2017/0309361 A1 Oct. 26, 2017

(30) Foreign Application Priority Data
Oct. 21, 2014 (EP) .................................. 14189638

(51) Int. Cl.
*A61B 6/03* (2006.01)
*A61B 6/00* (2006.01)
*G21K 1/10* (2006.01)
*G21K 5/04* (2006.01)
(Continued)

(52) U.S. Cl.
CPC ................ *G21K 1/10* (2013.01); *A61B 6/035* (2013.01); *A61B 6/06* (2013.01); *A61B 6/466* (2013.01); *G21K 5/04* (2013.01); *A61B 6/032* (2013.01); *A61B 6/4441* (2013.01)

(58) Field of Classification Search
CPC .......... A61B 6/032; A61B 6/035; A61B 6/06; A61B 6/4441; A61B 6/466; G21K 1/10; G21K 5/04
See application file for complete search history.

(56) References Cited

U.S. PATENT DOCUMENTS

| 4,980,904 A | 12/1990 | Sones |
| 7,082,189 B2 | 7/2006 | Yahata |
| 9,295,437 B2 | 3/2016 | Saito |

(Continued)

FOREIGN PATENT DOCUMENTS

| DE | 10227808 | 1/2004 |
| DE | 102012217616 | 3/2014 |

(Continued)

OTHER PUBLICATIONS

Hsieh, et al., "Enabling Photon Counting Detectors with Dynamic Attenuators", Medical Physics, 41, Feb. 19, 2010 (2014).

(Continued)

*Primary Examiner* — Mark R Gaworecki
(74) *Attorney, Agent, or Firm* — Larry Liberchuk

(57) ABSTRACT

The present invention presents a beam shaper for radiation imaging comprising a hollow beam shaper body filled with radiation attenuating gas. Radiation attenuation can be changed by adding or removing pressure to the gas or the housing containing the gas, making it suitable for use as a dynamic beam shaper in 3D radiation imaging.

13 Claims, 6 Drawing Sheets

(51) Int. Cl.
*G21K 1/04* (2006.01)
*A61B 6/06* (2006.01)

(56) References Cited

U.S. PATENT DOCUMENTS

2014/0294139 A1  10/2014  Funk
2014/0328453 A1* 11/2014  Hsieh .................... A61B 6/035
                                                           378/16

FOREIGN PATENT DOCUMENTS

| | | |
|---|---|---|
| DE | 102012223748 | 6/2014 |
| JP | S61142495 A | 6/1986 |
| JP | S63113551 A | 5/1988 |
| WO | 2013132361 | 9/2013 |
| WO | 2014072153 | 5/2014 |

OTHER PUBLICATIONS

Hsieh, et al., "Dose reduction using a dynamic, piecewise-linear attenuator", Med. Phys. 41 (2), Feb. 2014.

* cited by examiner

DYNAMIC BEAM SHAPER

CROSS REFERENCE TO RELATED APPLICATIONS

This application is the U.S. National Phase application under 35 U.S.C. § 371 of International Application No. PCT/EP2015/072502, filed Sep. 30, 2015, published as WO 2016/062504 on Apr. 28, 2016, which claims the benefit of European Patent Application Number 14189638.1 filed Oct. 21, 2014. These applications are hereby incorporated by reference herein.

FIELD OF THE INVENTION

The present invention generally relates to a dynamic beam shaper for a 3D imaging system, to a method to attenuate a radiation beam with a dynamic beam shaper and to a 3D imaging system.

BACKGROUND OF THE INVENTION

In 3D radiation imaging (see FIG. 1), such as computed x-ray tomography or 3D interventional x-ray imaging, projection images of a subject are acquired from different viewpoints and volumetric image data is reconstructed out of the acquired projections. If a spatially isotropic resolution is desired the angular range of the information content in the projection images has to span 180° plus a fan angle of the radiation beam. In most, if not all, current 3D radiation imaging systems a certain field of view of the subject is illuminated by an x-ray beam spanning a certain fan angle. To reduce radiation received by a subject the beam is usually filtered by a radiation filter, usually a homogeneous radiation absorbing solid or liquid, but also, less common, a homogeneous gas-filled x-ray filter as disclosed in DE 102 27 808 A1. Because attenuation of the x-ray beam is strongly dependent on a local thickness of a subject to be imaged (such as a patient body), thinner parts (e.g. edges) of the subject are over illuminated with respect to thicker parts. Furthermore typical object or patient shapes are not cylindrical so the optimal collimation of the x-ray beam depends on an angular direction of each projection.

To overcome this problem beam shapers are known. These are x-ray filtering devices that are able to shape the x-ray beam depending on the angular direction of each projection. The most common beam shaper is a so-called bow-tie filter, called as such due to its shape. Bow-tie filters attenuate more x-rays at the outside and less on the inside of the filter, thereby reducing x-ray dose on the edges of the subject. However, such beam shapers have certain shortcomings for use in 3D imaging systems. This is illustrated with the help of FIGS. 2a and 2b.

FIG. 2a zooms in on an active area of a 3D imager 10, 10'. The subject to be imaged 30 is placed between a radiation source 11 and a detector 12 in an examination region 14. The subject 30 is imaged with an (x-ray) radiation beam 13 emitted from the source 11 towards the detector 12. A bow-tie shaped beam shaper 20 is placed between the source 11 and the examining region 14. The beam shaper 20 comprises a radiation absorbing material. The radiation beam 13 is filtered such that photons in the center encounter less radiation absorbing material than photons on the sides. Subject 30 is shaped such that it is thicker at the center and thinner on the sides (as is usually the case for a human body). The center of the subject 30 receives a higher radiation dose than the sides due to bow-tie shape of the beam shaper 20 to account for the additional mass present at the center compared to the sides. The situation shown in FIG. 2a depicts a first extreme situation: the subject substantially covers the entire radiation beam 13. Individual beams 131, 132 and 133 are all (partly) absorbed by the subject 30. Because of this and because the outer beams 131 and 133 are filtered more strongly by the beam shaper 20 and encounter less mass of the subject than the center beam 132 a homogeneous intensity profile is achieved at the detector.

This is an ideal situation in case the subject is symmetric at all irradiation angles. However, in 3D imaging of a non-symmetric subject (such as shown in FIGS. 2a and 2b or in case of a human being), a non-ideal situation occurs. FIG. 2b depicts a second extreme situation: the radiation source 11 rotated to a position where the radiation beam 13 irradiates the subject 30 on its narrowest side. The subject 30 now does not cover the entire radiation beam. The center beam 132 is still fully attenuated by the subject 30, but a path through the subject 30 is much longer than in the situation of FIG. 2a, causing more attenuation and less radiation received by the detector 12, potentially resulting in decreased image quality. On the other hand, outer radiation beams 131 and 133 do not encounter the subject 30 at all and reach the detector 12 without any further attenuation after the beam shaper 20. The intensity profile at the detector is strongly out of balance: the sides of the detector 12 are over-illuminated, while the center is potentially under-illuminated. For this position a different beam shaper configuration would be desirable, e.g. one that is thinner in the center and thicker at the edges than the one shown in FIGS. 2a and 2b.

An optimal beam shaper configuration changes for each position (or at least multiple positions) of the radiation source 11 with respect to the subject 30 and therefore dynamic beam shapers were developed. These can take into account the angular inhomogeneity of the thickness of the subject. However, known dynamic beam shaping devices might not be usable during all operating modes of 3D radiation systems.

First, hard (i.e. high contrast) edges of an x-ray beam shaper lead to high contrast shadows on the projection images which has implications for the reconstruction algorithms. Second, a very high reproducibility of the attenuation profile is necessary in order to allow for a 3D (tomographic) reconstruction and consistent image quality, which is very challenging for known dynamic beam shapers. Third, depending on the position, the x-ray beam has to be attenuated to as low as 10%-20% of the original intensity. The amount of scattered radiation which is generated due to this absorption process can be significant and strongly depends on the actual choice of the filter material. Scattered x-ray radiation generally decorates the contrast of the projection images. And fourth, dynamic beam shapers need to be able to vary the x-ray beam profile fast enough to account for the fast rotation of state of the art 3D imaging systems. With known dynamic beam shapers this has proven to be rather challenging in combination with the previously stated other issues.

Several dynamic beam shapers for 3D x-ray imagers have been proposed, for instance in DE 10 2012 2217616 A1 or DE 10 2012 223748 A1. In these disclosures a dynamic beam filter is based on pumping liquid into the filter. However, these and other known dynamic beam shapers, are limited by the abovementioned technical issues to different extent, especially matching attenuation with the rotation speed of the source. Also, leakage of the liquid may cause serious damage to the electronics or mechanics of underlying equipment or parts. Because of these reasons these known dynamic beam shapers have not yet found significant clinical and commercial acceptance.

SUMMARY OF THE INVENTION

It is the aim of the present invention to overcome the above-stated technical issues, at least to a better extent, then the currently known dynamic beam shapers and as such to gain market and clinical acceptance.

A first embodiment according to the present invention are directed to a dynamic beam shaper for an imaging system according to claim 1. An advantage of using radiation absorbing gas to attenuate radiation is that leakage will potentially not have adverse effects. Also, weight of the beam shaper may be reduced.

In the context of this invention the term 'pressure inducing means' covers any means that induce pressure, directly or indirectly, to the hollow beam shaper body whether by inducing pressure from the outside or from the inside. By inducing pressure to the beam shaper body an attenuation profile of the gas can be changed by (locally) increasing or reducing an amount of gas molecules in the path of an x-ray beam.

The term 'the attenuation profile varies locally within the beam shaper body' means, in the context of this invention, that there is no homogeneous attenuation profile over the length of the beam shaper in the path of the radiation beam. In the present invention the intensity profile changes along the length of beam shaper in the apth of the radiation beam, for instance a gradual change or one or discrete local changes.

A further embodiment of the present invention is directed towards a beam shaper according to claim 2. A rigid housing is mechanically strong and can remain relatively non-complex and is similar to most known beam shapers. A bow-tie shape is a common shape for beam shaper that can deliver a homogeneous intensity profile for subjects that are thicker at the center and thinner at the edges (as is the case for, for instance, most human bodies).

A further embodiment of the present invention is directed towards a beam shaper according to claim 3. A flexible housing filled with attenuating gas may be manipulated into different shapes to allow for different path lengths through the beam shaper body and influencing the attenuation of radiation beams. Manipulation may be effected with a beam shaper body manipulator as is described in claim 4. The beam shaper body manipulator may manipulate the beam shaper body over its whole surface or may manipulate at one or more discrete surfaces (as is claimed in claim 5). An advantage of the latter embodiment is that the beam shaper body can be manipulated into very specific shapes, such as, for instance, a bow-tie or dumbbell shape.

A further embodiment of the present invention is directed towards a beam shaper according to claim 6. By adding or removing gas to or from the beam shaper body the amount of attenuating gas molecules in the beam shaper body is increased or decreased. In a rigid beam shaper body housing the pressure increases, while a flexible housing may be inflated into a desired shape. The gas flow control means could be a valve, a pump, a vent, combinations thereof or any other known means to control flow of gas between two chambers.

A further embodiment of the present invention is directed towards a beam shaper according to claim 7. Xenon is a particularly suitable gas which already sufficiently attenuates radiation at atmospheric pressure in a practically sized beam shaper body. Krypton requires a higher operating pressure and/or a larger housing making it slightly less ideal than Xenon, but beam hardening effects are reduced when Krypton is used as the radiation attenuating gas. A mixture of both gases could be used to optimize between advantages of each of the gases.

A further embodiment of the present invention is directed towards a beam shaper according to claim 8. In this way an attenuation profile can be determined (and set) to a determined body profile, resulting in an optimally tuned received radiation intensity for each part of a scanned subject.

Further embodiments of the present invention are directed towards a corresponding method according to any of the claims 9 to 14. Particularly the method of claim 14 makes the beam shaper suitable for use with 3D imaging systems, since the attenuation profile of the beam shaper can be adjusted according to a position of the source with respect to the examining region (and a shape of a subject to be imaged).

Further embodiments of the present invention are directed towards a 3D imaging system according to claim 15 comprising a dynamic beam shaper according to the present invention.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention.

To better visualize certain features may be omitted or dimensions may be not be according to scale.

DETAILED DESCRIPTION OF EMBODIMENTS

Figure 1A:
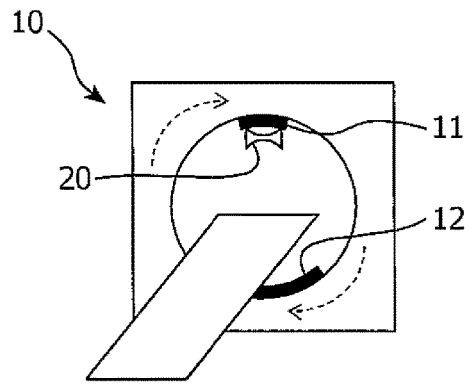
FIG. 1 schematic depicts of two exemplary 3D radiation imagers: a computed tomography device (la) and a 3D X-Ray imaging device (1*b*).
Figure 1B:
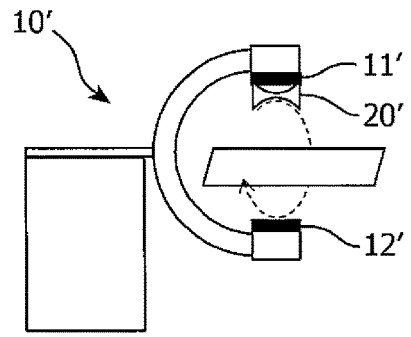

The invention is explained by 3D radiation imaging, especially, but not limited to, x-ray imaging, and in particular computed tomography (schematically depicted in FIG. 1a) and 3D X-Ray imaging (schematically depicted in FIG. 1b), where use is made of a radiation source 11, 11' emitting radiation through an examination region 14 towards a radiation detector 12, 12'. A beam shaper 20, 20' is placed near the source 11, 11' to attenuate a radiation beam before it reaches the examination region 14. A subject to be imaged 30, such as an animal or human body, e.g. for medical reasons, or an object, e.g. for security reasons), is moved through the examination region. The emitted radiation is attenuated in different levels by different body parts within the body and after detection it is processed and reconstructed into an image slice of the irradiated section of the body. This is repeated until the body, or at least the body part of interest, has been fully imaged. The resulting series of image slices may be combined to construct a three-dimensional image of the body and its internal hard and soft body parts.

The present invention is based on the insight that a radiation beam may be attenuated with a gaseous radiation absorbing material and that attenuation at different levels may be achieved by changing an amount of gas molecules in the path of the radiation beam. In the following various, non-limiting, embodiments of a dynamic beam shaper according to the present invention are described to illustrate this principle.

A first embodiment of a beam shaper according to the present invention comprises a hollow beam shaper body 21 filled with a radiation absorbing gas 22. The gas and the gas pressure may be chosen such that it attenuates radiation at any predetermined level. Such a beam shaper may already be used advantageously in a 2D imaging system instead of known beam shaping devices, for instance because the beam shaper according to present invention is lighter or potentially cheaper. Also, with a gas-filled beam shaper the intensity profile of the radiation beam may be adjusted to different shapes without mounting different devices (when used in combination with one of the following embodiments). And, the beam shaper may not have to be removed when switching from 2D-mode to 3D-mode (e.g. for C-arc systems).

However, it especially advantageous to use a gas filled beam shaper as a dynamic beam shaper for 3D imaging. In general, the following embodiments and concepts overcome the previously mentioned drawbacks of known dynamic beam shapers. For instance, changing the amount of gas molecules in the path of radiation beams can be done very fast such that this is fast enough to account for the rotation of the radiation source, which is usually in the order of 4 rotations per second. Also gas can be manipulated in a very reproducible and precise manner, which allows tomographic reconstruction and consistent image quality. Also, with a gas a desired attenuation profile of the beam shaper, e.g. a bowtie profile, can be obtained in various ways by locally changing the attenuation strength, as will be shown further on. Furthermore, when the beam shaper is damaged and gas escapes, there is a much smaller chance of damage to surrounding equipment and electronics, compared to liquid-based dynamic beam shapers. Other advantages, where applicable, are discussed for each of the embodiments.

Figure 3:
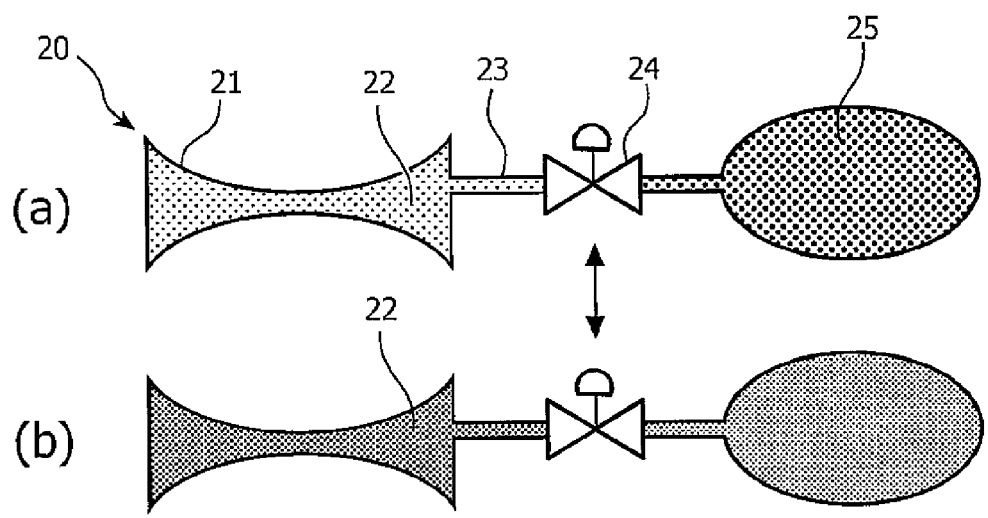
FIG. 3 schematically shows a first embodiment of a beam shaper according to the present invention.

A second embodiment of a beam shaper according to the present invention is depicted in FIG. 3. Beam shaper 20 comprises a rigid hollow beam shaper body 21, which is filled with a radiation absorbing gas at an initial gas pressure p1. The hollow body 21 is connected to a gas reservoir 25 by gas conduit 23. Gas reservoir 25 is filled with the same gas 22 as in the hollow body 21, but at a different pressure p2. The gas reservoir may have any dimension or shape. The conduit 23 comprises a valve 24 to influence gas flow between the reservoir 25 and the hollow body 23. A two-way gas pump (not shown) may be used instead of or in combination with the valve 24. An advantage of a rigid beam shaper body is that it is similar to known beam shapers and that mechanical complexity is limited.

In situation (a) gas pressure p1 in the hollow beam shaper body 21 is lower than gas pressure p2 in the gas reservoir 25. Opening the valve 24 causes gas to flow from the reservoir 25 to the hollow body 21 causes that the gas pressure p1 in the rigid hollow body 21 increases, as is shown in situation (b). Since there are now more gas molecules present in the beam shaper body 21, more radiation is attenuated by the beam filter. When gas is pumped out of the hollow beam shaper body the attenuation is lowered. Gas flow in and out of the beam shaper body 21 may be regulated, stepwise or continuous, such that it matches rotation of the detector 12 around the examination region and tuned such that it irradiates a subject 30 with differently attenuated irradiation from different irradiation angles to account for non-symmetric subjects.

A third series of embodiments of the beam shaper according to the present invention is depicted in FIGS. 4, 5, 6 and 7. In all these figures, situation (a) shows a beam shaper 20 comprising a flexible beam shaper body 21 at an initial low pressure p1, here depicted as a flat balloon-like structure, but it could have any other shape or pressure. As in the previous embodiment, the beam shaper body 21 is connected to a gas reservoir 25 with a gas conduit 23 with a valve 24 (and/or a pump). Gas may be supplied to the flexible beam shaper body 21 by opening the valve (or pumping). The flexible body 21 inflates upon receiving the gas. Radiation attenuation is increased when more gas is present in the flexible housing. As with the previously described embodiment, gas flow may be cyclically regulated to match source rotation.

It is usually desired to obtain a bow-tie-like shape. A flexible beam shaper body can obviously already be pre-shaped into a bow-tie (or any other desired) shape, but also other ways of achieving this can be achieved. Each of FIGS. 4, 5, 6 and 7 provides an alternate embodiment to achieve a bow-tie shape. A skilled person could easily find varying or other embodiments based that would work as well.

Figure 2A:
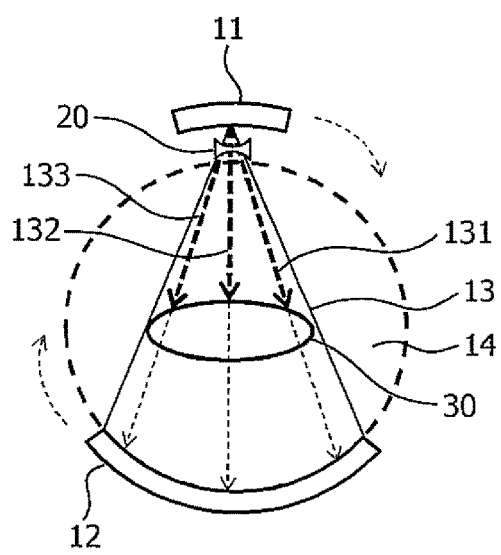
FIG. 2 schematically shows the positioning of a beam shaper between a detector and an examination region in two scan positions (2*a*: illuminating a wide side of a subject; 2*b*: illuminating a narrow side of the subject).
Figure 2B:
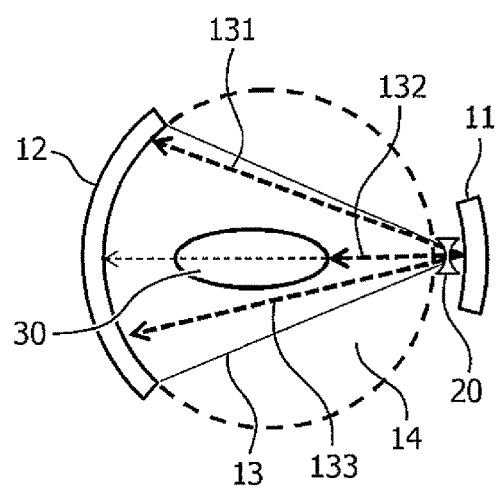
Figure 4:
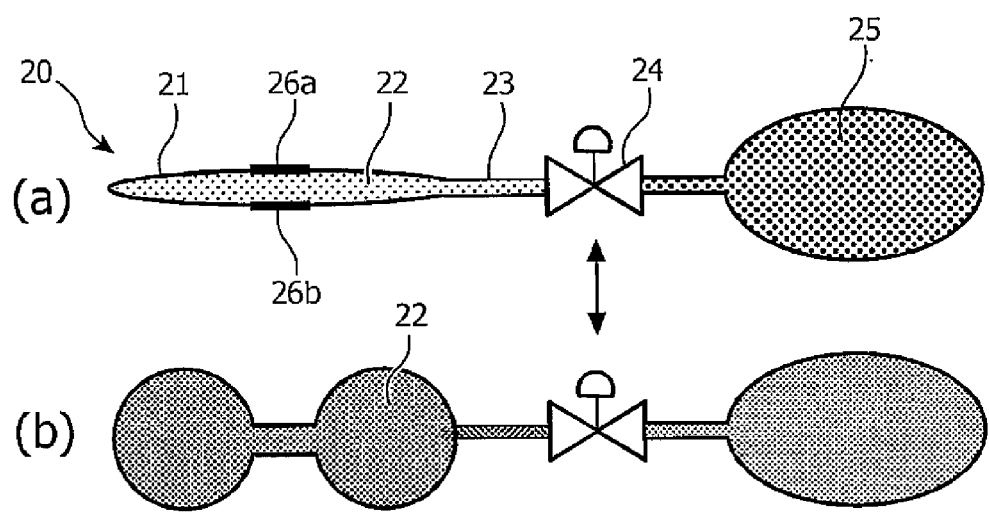
FIG. 4 schematically shows a second embodiment of a beam shaper according to the present invention.

In FIG. 4 the flexible beam shaper body 21 comprises a thickened part 26a, 26b at a central section of the beam shaper body 21. This thickened part 26a, 26b may be two (or more) discrete thickenings or one continuous ring-shaped thickening around the beam shaper body 21. When the beam shaper body 21 is inflated, the central section of is more resistant to the added pressure and will not expand (or least expand only a little), while the non-thickened outer sections expand more (situation (b)). This results in a dumbbell-like shape, similar to a bow-tie shape, that may be quite suitable to attenuate optimally according to the configuration shown in FIG. 2b: attenuation is minimal at the center and blocked strongly at the outsides. Variations on this are easily thought of, e.g. more areas that contain a thickening to force the beam shaper body 21 into a different shape or restricting expansion in certain directions (e.g. the sides) to obtain a different shape.

Figure 5:
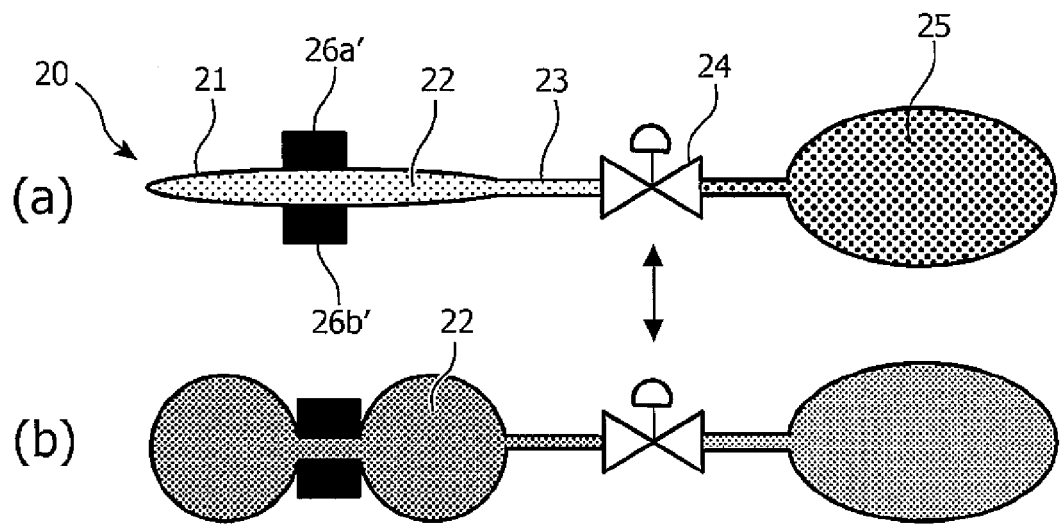
FIG. 5 schematically shows a third embodiment of a beam shaper according to the present invention.

FIG. 5 shows a similar embodiment, except in this case blocking elements 26a', 26b' are located above, below and/or around a central section of the beam shaper body 21. Upon inflation the beam shaper body 21 is restricted from expansion by the blocking elements 26a', 26b' at the central section, while at the non-restricted ends the beam shaper body 21 is free to expand, again resulting into a dumbbell-like shape.

Figure 6:
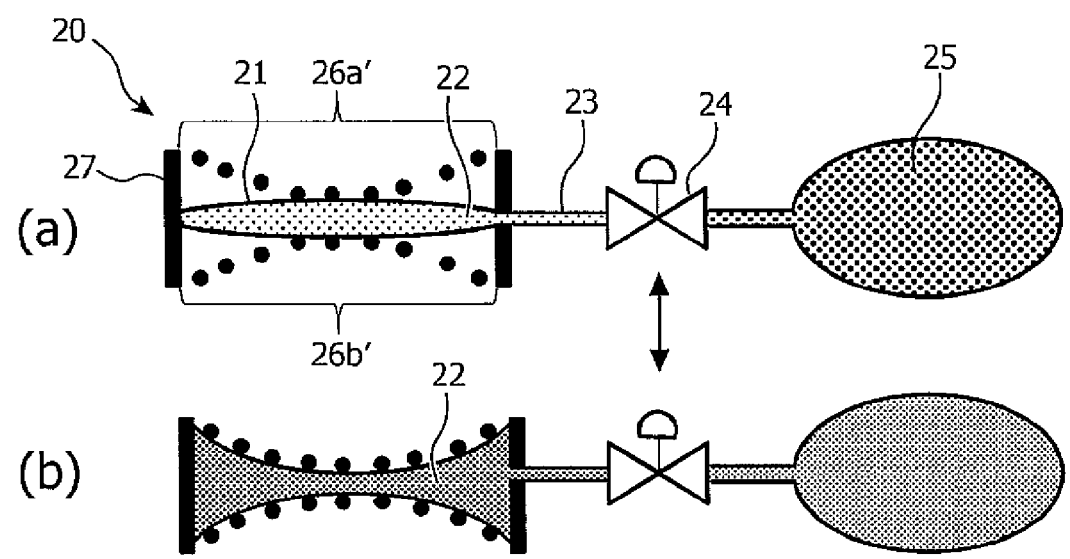
FIG. 6 schematically shows a fourth embodiment of a beam shaper according to the present invention.

FIG. 6 shows a variation on the embodiment of FIG. 5, wherein a series of blocking elements 26a', 26b' and end blocking elements 27 are placed along the flexible housing 21, such that upon inflation the beam shaper body 21 is forced into a bow-tie shape.

Figure 7:
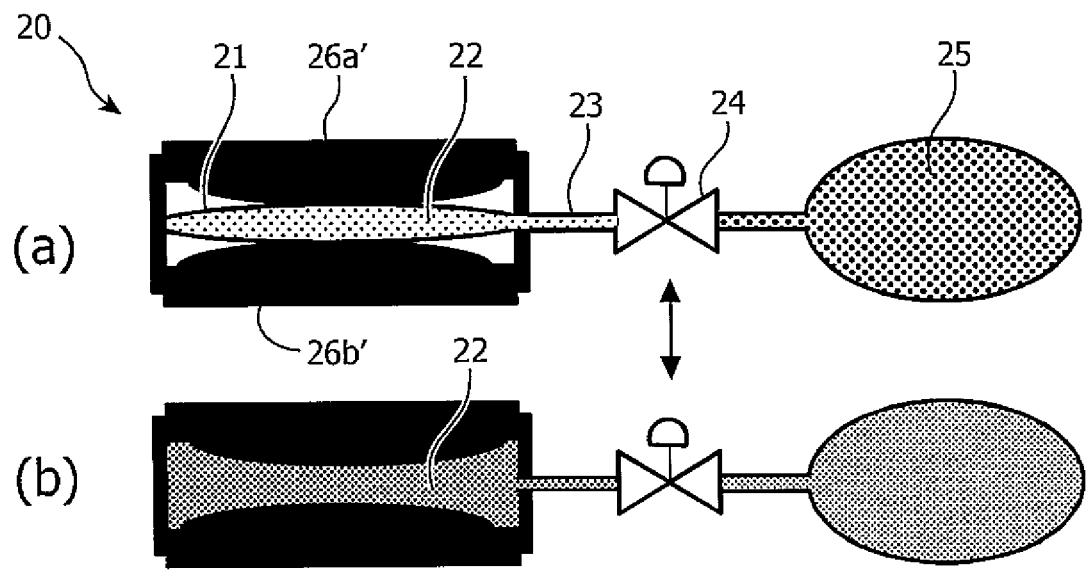
FIG. 7 schematically shows a fifth embodiment of a beam shaper according to the present invention.

FIG. 7 shows an even further variation wherein the individual blocking elements are formed into a continuous, bow-tie-shaped chamber surrounding the flexible beam shaper body 21. Blocking elements 26a', 26b' may be replaceably mounted to allow for interchanging them with differently shaped blocking elements that match other subject dimensions.

Figure 8:
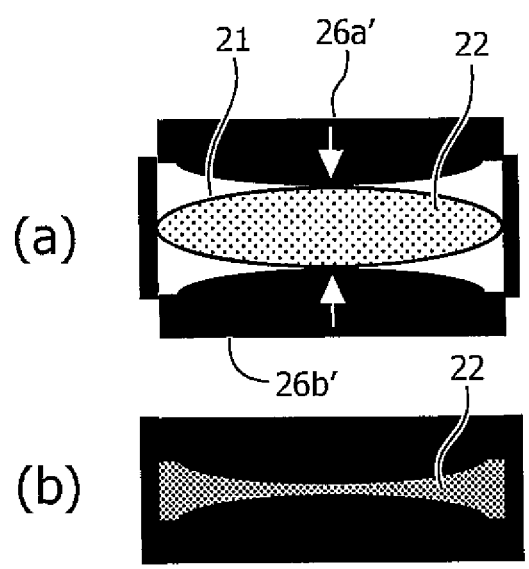
FIG. 8 schematically shows a sixth embodiment of a beam shaper according to the present invention.

FIG. 8 depicts an embodiment with similar blocking elements as in the previous embodiment, but in this embodiment the flexible beam shaper body 21 is not connected to a gas reservoir. In this case the blocking elements 26a', 26b' are movable towards and away from the beam shaper body 21, thereby compressing the beam shaper body into a bow-tie shape.

Figure 9:
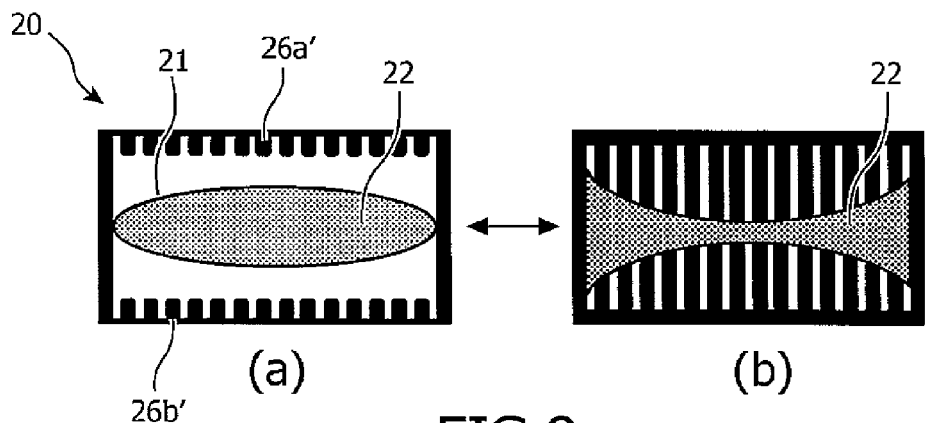
FIG. 9 schematically shows a seventh embodiment of a beam shaper according to the present invention.

FIG. 9 depicts another embodiment of the present invention wherein the flexible beam shaper body 21 is not connected to a gas reservoir. In this embodiment manipulators 26a', 26b', in this embodiment a series of rod-like structures, for instance telescopic rod-like structures, are positioned around the beam shaper body 21. The manipulators 26a', 26b' are individually extendable towards the flexible housing 21. Upon contact the manipulators 26a', 26b' deform the flexible housing 21. In situation (b) it is shown how a bow-tie shape is achieved with this embodiment. An advantage of this embodiment is that it provides flexibility to obtain any desired shape.

Figure 10:
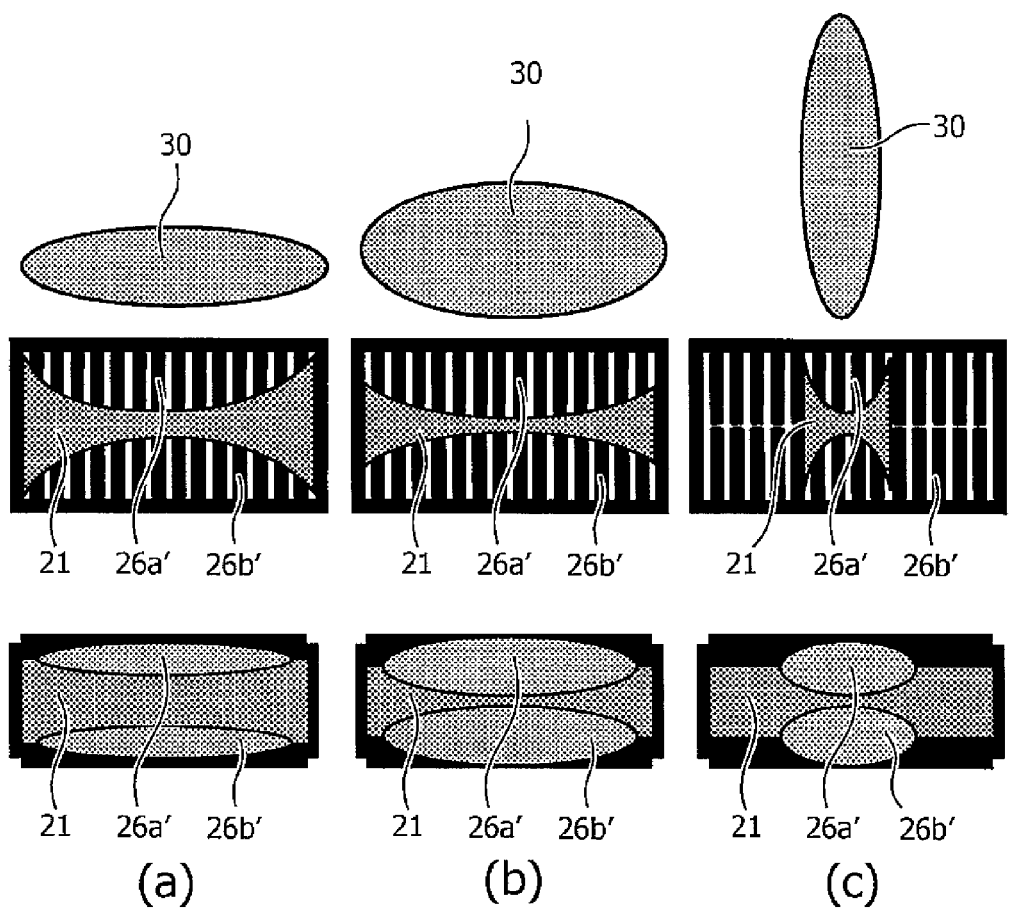
FIG. 10 schematically shows how a beam shaper according to the present invention may be adapted based on a determined body type.

In FIG. 10 this is shown in more detail. Depending on a body profile of a subject 30, the beam shaper body may be manipulated into a different (bow-tie) shape. For instance a bow-tie filter may be formed thicker for a thinner subject (situation (a)) than for a thicker subject (situation (b)). In 3D imaging the bow-tie filter may be formed as shown in situation (a) for a source 11 positioned to illuminating a broad area of the subject 30, while it may be formed as shown in situation (c) for when the source is positioned such that it illuminates a narrow area of the subject and the bow-tie filter should be thinner in the center and block as much as possible at the outside areas to avoid over-illumination at the edges of the detector 12. By matching movement of the manipulators 26a, 26b' with rotation of the source 11, a truly dynamic beam shaper could be obtained that results in a homogeneous intensity profile at the detector for all irradiation angles. However, technical realization of this embodiment is likely more difficult to practically achieve than the previously discussed embodiments, due to its complex shape and individual steering of the manipulators and because the manipulators need to be of a material that is transparent to the wavelength of the radiation.

As is shown in the lower row of FIG. 10, a similar effect may be achieved in a somewhat simpler manner with blocking elements 26a', 26b', similar to those described with the embodiment shown in FIG. 8, but wherein the blocking elements themselves are deformable into different shapes (e.g. by filling them with a gas with low atomic number or a liquid).

A good choice of radiation absorption gas is very important. A gas should be capable of attenuating radiation up to 80 to 90% within a relatively small volume. Many gases are not suitable for this reason, since they would require very large volumes or extremely high pressure to achieve this, which is practically not possible and/or undesirable. Also, it would be desirable to refrain from hazardous (e.g. toxic, corrosive or radio-active) gases which may cause problems with equipment, electronics or the subject to be imaged if a leak occurs.

Extensive screening was performed to determine suitable gases for use with a beam shaper of the present invention. First a filter thickness corresponding to attenuation of integrated primary x-ray intensity to 30% was calculated, assuming a 1 atmosphere pressure for the tested gases and using an x-ray spectrum of a tungsten anode (10 degree anode angle) at 100 keV, prehardened by a 2.7 mm Al filter in order to attenuate the low energy part of the spectrum. A lower filter thickness means a gas is more suitable for use with a beam shaper of the present invention. A high thickness would necessitate a large filter, which is practically problematic or a high pressure would be necessary, which would require high structural demands of the beam shaper body or could be hazardous. Further, a ratio of scattered to primary radiation (SPR) was determined by analytical estimations. These estimations are based on various assumptions and may depend on various boundary conditions, such as for instance the system geometry. Using different assumptions or boundary conditions may result in different values. Selected results for various gases are presented in table 1. Even though the same assumptions and boundary conditions were used for each gas, the presented values are only provided to illustrate comparisons between different gases and should be considered as arbitrary units (a.u.).

TABLE 1

Gas screening results

| Element | Filter thickness (mm) | SPR (a.u.) |
| --- | --- | --- |
| Hydrogen | 380016 | 2.2 |
| Xenon | 103 | 3.3 |
| Krypton | 688 | 3.9 |
| Radium | 131 | 4.6 |
| Helium | 370179 | 5.0 |
| Argon | 8763 | 10.0 |
| Chlorine | 5286 | 11.3 |
| Nitrogen | 43482 | 13.4 |
| Oxygen | 34270 | 15.8 |
| Fluoride | 27325 | 16.6 |
| Neon | 43855 | 17.0 |

Table 2 provides comparative results for commonly used (solid) aluminum- or carbon-based (e.g. teflon) beam shapers. Filter thickness and SPR were determined similarly to those of the gases of table 1.

TABLE 2

Solid beam shaper materials screening results

| Element | Filter thickness (mm) | SPR (a.u.) |
| --- | --- | --- |
| Carbon | 26.1 | 13.2 |
| Aluminum | 10.4 | 13.3 |

Gases with a calculated filter thickness higher than 1000 mm would be impractical or require a very high pressure and therefore are less preferred in light of the present invention.

Radium has a relatively low filter thickness and a low SPR, but is unsuitable due to its radioactivity.

Xenon is the most preferred gas when a good balance between thickness and gas pressure is desired. It combines a low filter thickness with a low SPR. While filter thickness is higher than that of the solid beam shapers, scattering properties (SPR) are significantly better and, obviously, provides all the previously mentioned advantages for a gas-based beam shaper. Absorption of x-ray radiation is generally described by Beer-Lambert's law: relative absorption is exponentially dependent on the path length. Therefore, in general terms, small changes of either gas pressure or filter thickness leads to strong changes of local x-ray attenuation. Because of this, only relatively small manipulations of the gas pressure in the beam shaper body (as in e.g. embodiments similar to FIGS. 3 to 7) or changes in the beam shaper body shape (a s in e.g. embodiments similar to FIGS. 8 to 10) are necessary to achieve necessary attenuation at a specific radiation angle. This facilitates fast and reproducible changes and limited structural complexity of the beam shaper. To achieve attenuation of a 100 keV x-ray spectrum (tungsten, as described previously) to 30% of the incident integral photon flux would require a path length of 10 cm through a beam shaper body filled with xenon at atmospheric pressure (1 atmosphere). Dimensions of such a beam shaper would fit well with current 3D imagers. Also, since pressure is close to 1 atmosphere (and as such close to atmospheric pressure), structural requirements of the beam shaper body are not critical. Furthermore, Xenon is a non-toxic noble gas that is inert to nearly all materials. An additional effect relates to the so-called K-edge (which is sudden increase of the attenuation coefficient as a function of energy) of the absorber material. If the K-edge of the absorber material lies within the energy range used for imaging purposes it will lead to an edge in the attenuated x-ray spectrum.

Krypton is also suitable for use. However, for approximately the same SPR, a 6.7 times larger filter thickness or pressure is necessary to achieve the same radiation attenuation. However, Krypton (atomic number (Z)=36) will have a lower beam hardening effect than Xenon (Z=56), because the spectrum of an attenuated beam shifts to higher photon energies for materials with a higher atomic number. Because of this a (somewhat) thicker beam shaper filled with Krypton at a pressure higher than atmospheric pressure could be a good alternative for a Xenon-filled beam shaper, should beam hardening become an issue. There are of course stronger structural requirements for the housing of course.

A mixture of gases, such as a Xenon-Krypton mixture, could be used to lower beam hardening for pure Xenon, while filter thickness or gas pressure can be kept lower than that of pure Krypton. It would be beneficial if a gas pressure could be kept below a threshold that would classify the beam shaper as a pressure vessel under regulatory requirements.

Mechanical construction of the beam shaper housing needs to be able to withstand a moderate pressure difference (e.g. between 0.95 atm and 2 atmosphere for an exemplary xenon absorber) without plastic deformation. Additional mechanical challenges may arise from the requirement for fast and cyclic pressure variations. The thickness of the beam shaper body housing material is on the other hand constrained by x-ray physical effects (attenuation, beam hardening and scattering). For a rough feasibility assessment a 2 mm thick carbon-fibre-reinforced plastic for both sides of the attenuator is suitable, as such a material will, generally only lead to a slight attenuation of the x-ray beam at excellent mechanical strength and rigidity. A passage through 4 mm carbon (2 mm on both sides of the filter housing) attenuates the integrated photon flux to 83%. A passage through 2 mm carbon (1 mm on both sides of the filter housing) will attenuate the integrated photon flux to 91%. This beam attenuation is, up to first order, spatially invariant. Owing to the low atomic number of carbon (Z=6) no significant beam hardening is expected for either case. A scatter to primary ratio on the order of SPR=2 a.u. is expected at the detector surface for a material thickness of 4 mm, a scatter to primary ratio on the order of SPR=1 a.u. is expected for a material thickness of 2 mm. These SPR values are again arbitrary units and were determined using the same boundary conditions and assumptions as with the gas screening. Other beam shaper body design parameters to consider include tuning the beam shaper to desired attenuation profiles for typical patient shapes and the allowable space for the beam shaper within the imaging device.

A further advantage of using gas-filled beam shapers is that "air calibration" of the imaging system (without bow-tie filter) can be strongly facilitated by exchanging the attenuating gas by air in the beam shaper. No mechanical movement of filter components is necessary. The idea of a gas based dynamic beam shaper can furthermore be combined with usual "rigid" beam shaping devices to minimize complexity. It may in particular be desirable to design the beam shaper body of the gas based attenuator such that its attenuation profile resembles the minimal attenuation variation that is generally needed at any angle.

Figure 11:
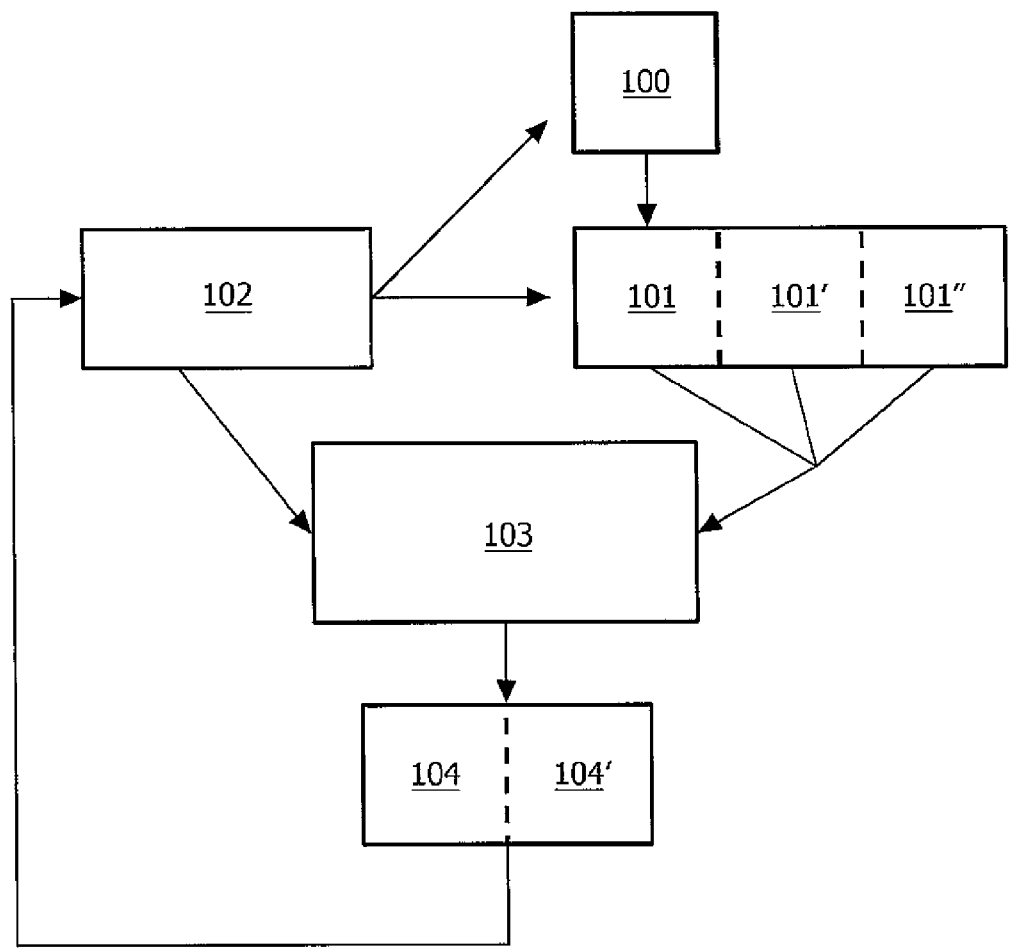
FIG. 11 schematically shows a method to attenuate a radiation beam with a beam shaper for an imaging system shaper according to the present invention.

In FIG. 11 a method according to the present invention is schematically depicted. A pressure is induced (103) to a beam shaper body based on various (optional) input parameters. For instance, a body profile for the subject to be imaged may be determined (100) and used (101) to select a desired beam shaper intensity profile, for instance selecting an intensity profile based on the body type (101), selecting a standard intensity profile (101'), such as for instance a bow-tie profile, or selecting another profile (101"). Also, a position of a radiation source may be determined (102) and be used as an input parameter for inducing pressure (103). Pressure maybe induced by adding or removing gas from the beam shaper body (104) or by adding external pressure to the beam shaper body (104') or both. In case of a radiation source moving around the subject, then this process can be repeated for each position of the source with respect to the subject.

While the invention has been illustrated and described in detail in the drawings and foregoing description, such illustration and description are to be considered illustrative or exemplary and not restrictive; the invention is not limited to the disclosed embodiments. For instance, pressure could potentially also be induced by non-mechanical means, such as by heating or cooling means, provided that gas expansion or contraction due to temperature changes is sufficiently fast and reproducible.

Dimensions may not be too scale. Certain features may have been enlarged, simplified or repositioned to more clearly illustrate the present invention.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A dynamic beam shaper for a 3D imaging system comprising:
   a hollow beam shaper body that has a flexible housing containing a radiation absorbing gas for attenuating radiation of a radiation beam;
   pressure inducer that is arranged to induce a pressure to the hollow beam shaper body, wherein an attenuation profile of the beam shaper body is adaptable based on the induced pressure, and wherein the attenuation profile varies locally within the beam shaper body such that there is no homogeneous attenuation profile over a length of the beam shaper body in a path of the radiation beam.

2. The beam shaper according to claim 1, wherein the pressure inducer comprises a beam shaper body manipulator for manipulating a shape of the flexible housing.

3. The beam shaper according to claim 2, wherein the beam shaper body manipulator comprises at least one manipulator element that is configured to manipulate the shape of the flexible housing at a discrete position on the flexible housing.

4. The beam shaper according to claim 1, wherein the pressure inducer comprises a gas container connected to an opening in the beam shaper body with a gas conduit and a gas flow controller configured to allow a controlled gas flow between the gas container and the beam shaper body.

5. The beam shaper according to claim 1, wherein the gas is Xenon, Krypton or a mixture thereof.

6. The beam shaper according to claim 1, further comprising:
   a body profile determiner configured to determine a body profile of a subject to be imaged; and
   an attenuation profile determiner configured to determine the attenuation profile of the beam shaper body based at least on the determined body profile.

7. A 3D imaging system comprising a dynamic beam shaper according to claim 1.

8. A method for attenuating a radiation beam for a 3D imaging system, comprising:
   providing a dynamic beam shaper that comprises a hollow beam shaper body that has a flexible housing containing a radiation absorbing gas for attenuating radiation of the radiation beam; and
   inducing a pressure to the hollow beam shaper body, wherein an attenuation profile of the beam shaper body is adapted based on the induced pressure, wherein the attenuation profile is varied locally within the beam shaper body such that there is no homogeneous attenuation profile over a length of the beam shaper body in a path of the radiation beam.

9. The method according to claim 8, wherein the pressure to the hollow beam shaper body is induced by manipulating a shape of the beam shaper body.

10. The method according to claim 9, wherein the shape of the beam shaper body is manipulated into a bow-tie shape.

11. The method according to claim 8, wherein a body profile is determined for a subject to be imaged and used as an input parameter for manipulating the shape of the beam shaper body.

12. The method according to claim 8, wherein the pressure to the hollow beam shaper body is induced by adding or removing the gas from the beam shaper body.

13. The method according to claim 8, wherein the pressure to be induced to the hollow beam shaper body is determined based on a position of the radiation source with respect to an examination region.

* * * * *